United States Patent [19]
Chichibu

[11] Patent Number: 5,019,498
[45] Date of Patent: May 28, 1991

[54] METHOD OF ASSAYING HIGH MOLECULAR HYALURONIC ACID AND KIT OF REAGENTS FOR SUCH ASSAY

[75] Inventor: Kenji Chichibu, Saitama, Japan

[73] Assignee: Chugai Seiyaku Kabushiki Kaiska, Tokyo, Japan

[21] Appl. No.: 162,672

[22] Filed: Mar. 1, 1988

[30] Foreign Application Priority Data

Mar. 3, 1987 [JP] Japan .................. 62-48518

[51] Int. Cl.$^5$ .................. G01N 33/535; G01N 33/53; G01N 33/566; G01N 33/543
[52] U.S. Cl. ...................... 435/7.5; 435/7.9; 435/7.94; 435/975; 436/501; 436/518; 436/808; 436/815; 436/524; 436/527; 436/529
[58] Field of Search .................. 435/7, 4, 810, , 174, 435/7.5, 7.9, 975; 436/501, 518, 815, 808, 811, 524, 527, 529, 509, 503, 827

[56] References Cited

U.S. PATENT DOCUMENTS 4,826,776  5/1989  Brandt et al. .................. 436/501

FOREIGN PATENT DOCUMENTS

WO8700289  1/1987  PCT Int'l Appl. .

OTHER PUBLICATIONS

Alberts, B., et al., in *Molecular Biology of the Cell*, published by Garland Publishing, New York, NY (1983) pp. 702–703.
Oellerich, M., *J. Clin. Chem. Clin. Biochem.*, vol. 22, 1984, pp. 895–904.
*Analytical Bio Chemistry*, vol. 109, 1980, pp. 386–394; Laurent et al, Determination of hyaluronate in biological samples by a specific radioassay technique.
*Chemical Abstracts*, vol. 107, No. 1, Jul. 1987, p. 345, col. 2, abstract No., Columbus, Ohio, U.S.; H. D. Keiser, A solid-phase immunoassay for the binding of cartiliage proteoglycan to hyaluronic acid, & ANAl. Biochem 1987, 160(2), 462–467.
*Chemical Abstracts*, vol. 88, No. 20, May 1978, p. 190, col. 1, abstract No. 147703g, Columbus, Ohio, U.S.; V. C. Hascall., Interaction of cartilage proteoglycans with hyaluronic acid, & J. Supramol. Struct. 1977, 7(1), 101–120.
Analytical Biochemistry. Determination of Hyaluronate in Biological Samples by a SpecificRadioassay Technique. 109, 386–394 (1980).
Analytical Biochemistry. Immunoenzymoassay of the Hyaluronic Acid-Hyaluronectin Interaction: Application to the Detection of . . . Cancer Patients. 149, 555–565 (1985).

*Primary Examiner*—Esther L. Kepplinger
*Assistant Examiner*—Toni R. Scheiner
*Attorney, Agent, or Firm*—Browdy and Neimark

[57] ABSTRACT

A high molecular hyaluronic acid which is an important factor in the diagnosis of inflammations such as rheumatism or diseases such as cancer is assayed as a complex of sandwich structure in which a hyaluronic acid binding protein is coupled to the hyaluronic acid of interest at two or more sites of binding without the need to employ a competitive reaction as in the prior art techniques of assay. The assay method of the present invention does not require a purified form of hyaluronic acid as a reagent and permits as small as 10 ng of a high molecular hyaluronic acid to be detected or quantified by a very simple operation.

12 Claims, 1 Drawing Sheet

METHOD OF ASSAYING HIGH MOLECULAR HYALURONIC ACID AND KIT OF REAGENTS FOR SUCH ASSAY

BACKGROUND OF THE INVENTION

The present invention relates to a method of assaying hyaluronic acid that is present in loose connective tissues such as synovial fluid in the articular cavity. The present invention also relates to a kit of reagents for assaying hyaluronic acid. More particularly, the present invention relates to a method capable of highly sensitive assaying of a high molecular weight hyaluronic acid, as well as a kit of reagents for performing such assay.

Hyaluronic acid, which is an acidic mucopolysaccharide composed of alternate polymerization of N-acetylglucosamine and glucuronic acid by β-1,4 bond, serves to bind subcutaneous tissues and is found in the umbilical cord, in synovial fluid in the articular cavity and in the crystalline lens of the eye.

It has been known that the blood level of hyaluronic acid increases in patients suffering from inflammations such as rheumatism or from diseases such as cancer. Therefore, quantitative determination of hyaluronic acid in blood has potential utility in clinical applications for the purpose of estimating the development of inflammations or a patient's progress in recuperating from surgical operations, or of diagnosing diseases such as cancer.

Quantitative determination of hyaluronic acid has conventionally been performed by radioassays employing hyaluronic acid binding proteins labelled with radioactive iodine or by immunoenzymoassays making use of hyaluronictin. In radioassays, a solid phase such as Sepharose coupled to hyaluronic acid is mixed with a sample containing hyaluronic acid to be assayed and the mixture is left to stand after addition of a hyaluronic acid binding protein labelled with radioactive iodine. In this method, the binding of Sepharose-coupled hyaluronic acid to the radiolabelled hyaluronic acid binding protein is inhibited to a degree that depends upon the concentration of hyaluronic acid in the sample. The concentration of hyaluronic acid in the sample can be determined indirectly by measuring the amount of radiolabelled hyaluronic acid binding protein.

Both the radioassays and immunoenzymoassays utilize a competitive reaction and the sensitivity of the assay of hyaluronic acid is not satisfactorily high, i.e., 40 ng at best. The conventional techniques also have the disadvantage that even a low molecular weight hyaluronic acid which has only one site for binding to hyaluronic acid binding proteins or hyaluronectin can participate in the competitive reaction. In other words, not only is the high molecular weight hyaluronic acid of interest assayed but also the physiologically unimportant low molecular weight hyaluronic acid. This presents a serious problem in diagnosis of inflammations such as rheumatism there hyaluronic acid of a comparatively high molecular weight is the substance to be measured. It has therefore been strongly desired to develop a method that is insensitive to a low molecular weight hyaluronic acid and which is yet capable of providing more sensitive assay of high molecular weight hyaluronic acid than the prior art techniques.

SUMMARY OF THE INVENTION

An object, therefore, of the present invention is to provide a method capable of selective and highly sensitive assay of a high molecular weight hyaluronic acid without depending upon a competitive reaction and without responding to any of the unwanted low molecular weight hyaluronic acids.

Another object of the present invention is to provide a kit of reagents suitable for accomplishing such assay of hyaluronic acid.

In order to attain these objects, the present inventors conducted intensive studies noting the fact that a physiologically important high-molecular weight hyaluronic acid has at least two sites for coupling with a hyaluronic acid binding protein. On the basis of this finding, the present inventors formed a complex of sandwich structure in which a hyaluronic acid binding protein was coupled at two or more sites to a hyaluronic acid having a sufficiently high molecular weight to permit coupling with the hyaluronic acid binding protein at two or more sites (this hyaluronic acid is hereinafter referred to as "a high molecular hyaluronic acid"), and measured the concentration of the so formed complex of sandwich structure. This method was found to be capable of determining the concentration of the high molecular hyaluronic acid of interest with high sensitivity.

In one aspect, the present invention provides a method of assaying a high molecular hyaluronic acid which comprises the following steps: adding a sample containing a hyaluronic acid of interest to a hyaluronic acid binding protein that is adsorbed on a solid phase, thereby permitting the adsorbed hyaluronic acid binding protein to bind to the hyaluronic acid of interest; further adding either a hyaluronic acid binding protein and a marker or a hyaluronic acid binding protein labelled with a marker, thereby forming a complex of sandwich structure in which the hyaluronic acid of interest is held between the solid phase adsorbed hyaluronic acid binding protein and the labelled hyaluronic acid binding protein; and measuring the quantity of said hyaluronic acid of interest in terms of the marker in said complex.

In another aspect, the present invention provides a kit of reagents suitable for implementing said assay method.

DETAILED DESCRIPTION OF THE INVENTION

Figure 1:
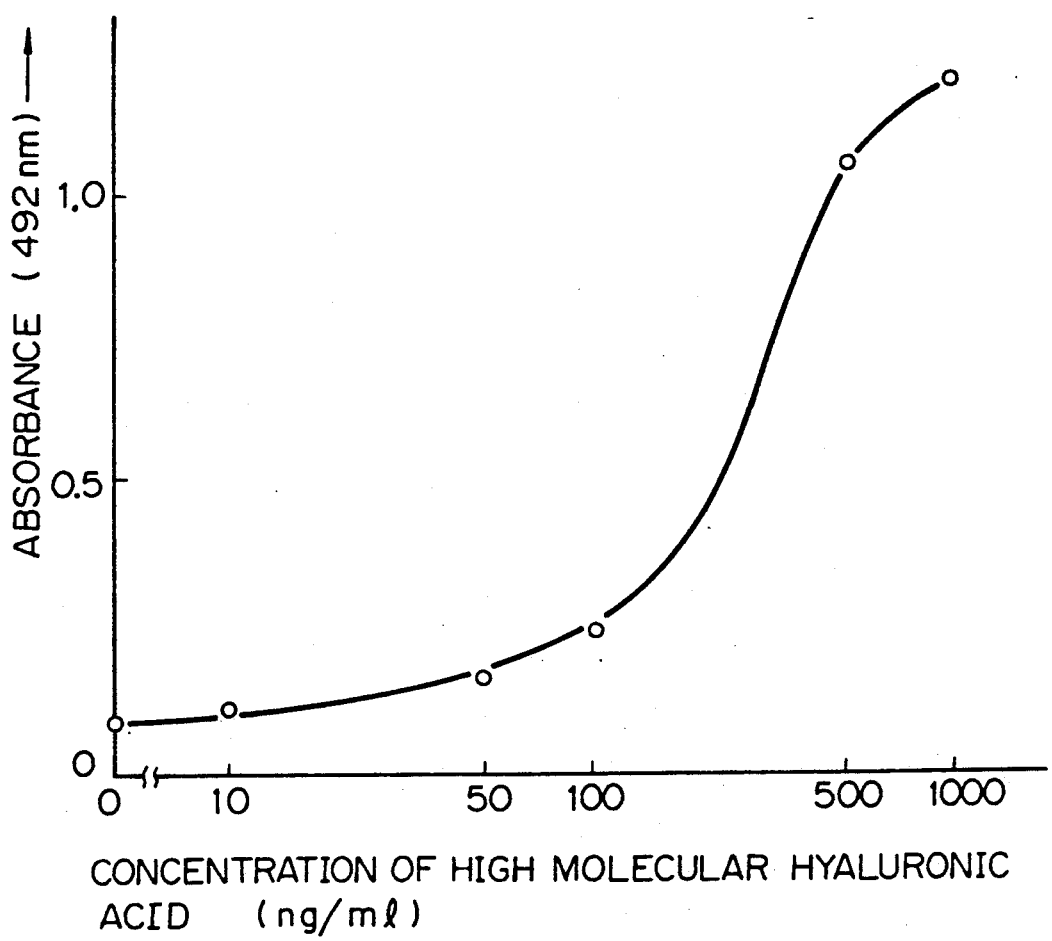
FIG. 1 is a graph showing the relationship between absorbance and the concentration of high molecular hyaluronic acid as obtained by the assay method of the present invention.

The assay method of the present invention starts with adsorbing a hyaluronic acid binding protein to the surface of a solid phase. The solid phase still has sites left on its surface which are capable of coupling with the hyaluronic acid binding protein or other molecular species, so upon addition of a sample to be assayed the high molecular hyaluronic acid of interest in the sample and other blood components might adhere to these sites. It is therefore recommended that prior to addition of the sample, a blocking substance be added so as to cover any part of the solid phase on which the hyaluronic acid binding protein has not been adsorbed. Illustrative blocking substances that may be employed are γ-globulin, serum albumin and serum extracted from cows and other animals. Bovine γ-globulin is advantageous when a Falcon plate is used as the solid phase.

In the next step, the sample containing a high molecular hyaluronic acid of interest is added to the solid phase on which the hyaluronic acid binding protein has been adsorbed. The sample to be added need not be the high molecular hyaluronic acid in a form isolated by extraction and a human blood or body fluid sample may be used as it is taken from the human body. If desired, the sample may be dissolved in a solution of a blocking substance or diluted serum before it is added to the solid phase on which the hyaluronic acid binding protein has been adsorbed.

After coupling the high molecular hyaluronic acid to the hyaluronic acid binding protein adsorbed on the solid phase, the surface of the solid phase is preferably washed.

In the third step of the process of the present invention, a hyaluronic acid binding protein labelled with a certain marker is added to the solid phase to which the high molecular hyaluronic acid has been coupled. Suitable markers include isotopes, fluorochromes, avidin, biotin, chemoluminescent substances and enzymes. Any other markers that are conventionally used to label high molecular weight materials may be used without limitation.

Alternatively, a proteinaceous substance that easily binds to a marker is preliminarily coupled to the hyaluronic acid binding protein, which is subsequently added to the solid phase (to which the high molecular hyaluronic acid has been coupled) together with a suitable marker.

By adding the hyaluronic acid binding protein in the third step, a complex of sandwich structure is formed in which the high molecular hyaluronic acid is held between the hyaluronic acid binding protein adsorbed on the solid phase and the labelled or easily labelable hyaluronic acid binding protein.

In the fourth step of the process of the present invention, the content of the marker in the complex of sandwich structure is measured to quantify the high molecular hyaluronic acid of interest. The complex of sandwich structure has the high molecular hyaluronic acid of interest incorporated therein but none of the low molecular hyaluronic acids that should not be assayed by the method of the present invention are capable of forming a sandwich structure of the nature described above. Therefore, by measuring the concentration of the marker on the surface of the solid phase, only the high molecular hyaluronic acid that is capable of forming the intended sandwich structure can be quantified.

The method for measuring the concentration of the marker depends on the type of the marker and if it is a chemoluminescent substance the absorbance of the solution that has undergone reaction with this substance may be measured.

In practicing the method of the present invention, it is advantageous to prepare samples containing known concentrations of a marker and a high molecular hyaluronic acid of interest and to construct calibration curves for the relationship between signal intensity and those known concentrations so that measured values can be corrected against these calibration curves.

Examples of the solid phase that can be used in the method of the present invention include plates, tubes, beads, membranes and gels. It should, however be noted that these are not the sole examples and any other solid phase on which the hyaluronic acid binding protein can be adsorbed are usable.

Examples of the hyaluronic acid binding protein that can be used in the present invention include the proteoglycan purified by A. E. Laurent et al. [see Analytical Biochemistry, 109, 386–394 (1980)], link protein, hyaluronectin, etc.

The substance to be assayed by the method of the present invention is a hyaluronic acid of comparatively high molecular weight which is considered to be an important factor for the diagnosis of inflammations such as rheumatism or diseases such as cancer, and it is necessary to prevent measurement of a low molecular hyaluronic acid that is outside the scope of assay by the present invention.

In the method of the present invention, the high molecular hyaluronic acid of interest is quantified as a complex of sandwich structure in which a hyaluronic acid binding protein is coupled to said hyaluronic acid at two or more sites. Therefore, the low molecular hyaluronic acids which have only one site for binding to the hyaluronic acid binding protein are unable to form a complex of sandwich structure of the nature described above and thus are insensitive to assay by the method of the present invention.

The prior art methods of assaying hyaluronic acid depend on a competitive reaction but the method of the present invention does not. Therefore, this method has the advantage that it does not require the use of hyaluronic acid as a preliminarily purified reagent and that it can be implemented with great ease.

The assay method of the present invention has such a high sensitivity that it is capable of detecting and quantifying the high molecular hyaluronic acid even if it is present in a trace amount of as small as 10 ng.

The following example is provided for the purpose of further illustrating the present invention but is in no way to be taken as limiting.

The following description consists of two parts, the first part relating to the method of preparing a purified hyaluronic acid binding protein to be used in the assay method of the present invention, and the second part describing construction of calibration curves by practicing the assay method of the present invention using samples containing known concentrations of high molecular hyaluronic acid.

In the following description, M signifies mol/L and % denotes g/100 ml.

Purification of Hyaluronic Acid Binding Protein

In order to extract and purify a hyaluronic acid binding protein for use in the present invention, the following procedures were taken in accordance with the method of A. E. Laurent et al. described in Analytical Biochemistry, 109, 386–94 (1980).

Bovine nasal cartilage (300 g; obtained from Tokyo Shibaura Zoki Co., Ltd.) was cut into small pieces with scissors, immersed in a 0.5 sodium acetate solution (pH 5.8) containing 4M guanidine hydrochloride (Wako Pure Chemical Industries, Ltd.) and which was held at 4° C. (this solution is hereinafter referred to as buffer solution A), and extracted with stirring overnight at 4° C.

After centrifugation for 20 minutes at 13,000 g, the supernatant was separated, dialyzed against distilled water and freeze-dried. The solids were crushed to obtain a crude extract powder.

The crude extract powder was treated with trypsin by the following procedures. The crude extract powder (1,600 mg) and 0.8 mg of trypsin (Sigma) were dissolved in 25 ml of a 0.1M Tris-HCl buffer solution (pH 7.3) containing 0.1M sodium acetate and the solution was held at 37° C. for 2 hours. After adding 1 mg of soybean trypsin inhibitor (Sigma) and 19.1 g of guanidine hydrochloride, a 0.5M sodium acetate solution was added to make a total volume of 50 ml.

The solution containing the trypsin-treated hyaluronic acid binding protein was subjected to affinity chromatography for the preparation of a purified hyaluronic acid binding protein by the following procedures.

Fifty milliliters of the solution containing the trypsin-treated hyaluronic acid binding protein was mixed with 50 ml of a separately prepared hyaluronic acid coupled Sepharose (for the method of its preparation, see below) and the mixture was immediately placed in a dialyzing membrane, followed by dialysis against 9 volumes of distilled water overnight at 4° C. After dialysis, the entire volume of the gel was packed in a column having an inside diameter of 3.2 cm. The column was washed with a 1M sodium chloride solution to remove the unadsorbate.

Unwanted protein was removed by successive washing with 1M-3M sodium chloride and the adsorbate was recovered by elution with buffer solution A.

The recovered fractions were concentrated with DIAFLO PM-10 (Amicon) to a total volume of 4 ml and passed through a Sepharose 6B column (3.1 cm$^\phi$×43 cm). The fractions showing second and third peaks were recovered, followed by separation and concentration with DIAFLO PM-10 to prepare reagents of hyaluronic acid binding protein.

Preparation of Hylaluronic Acid Coupled Sepharose p

A water-soluble carbodiimide (1.4 g) was added to a mixture of 600 mg of sodium hyaluronate (Seikagaku Fine Biochemicals), 75 ml of AH-Sepharose (Pharmacia Fine Chemicals) and 200 ml of distilled water, and the mixture was left to stand at room temperature for 24 hours. The reaction was terminated by addition of 10 ml of acetic acid. The resulting gel was recovered and successively washed with 1,000 ml each of 1M NaCl, 0.1M Tris-HCl (pH 8.1) containing 1M NaCl, 0.05M formate ester (pH 3.1), distilled water, and 0.5M sodium acetate (pH 5.7) to obtain a hyaluronic acid bound Sepharose.

Preparation of Biotin-Hyaluronic Acid Binding Protein Complex

The hyaluronic acid binding protein was coupled to biotin by the following procedures as a preliminary step for coupling with a marker POD.

To 1 mg of a solution of a hyaluronic acid binding protein in 1 ml of NaHCO$_3$, biotin-O-Su (obtained from PIERCE Chemical Company) was added in an amount of 1 mg in 1 ml of dimethyl sulfoxide and the mixture was stored at room temperature for 4 hours.

The solution was passed through Sephadex G 25 packed in a column (Columns PD-10) which was equilibrated with a 10 mM sodium phosphate buffer solution (pH 7.4) containing 0.1% NaN$_3$ and 0.9% NaCl (this solution is hereinafter referred to as PBS).

The protein fractions were recovered, mixed with 1.53 g of guanidine hydrochloride and charged into a suspension of hyaluronic acid coupling Sepharose gel that had been prepared by mixing a hyaluronic acid coupled Sepharose gel (10 ml wet volume) with 40 ml of a buffer solution (25 mM sodium phosphate containing 1.5M NaCl; pH 7.0) containing 0.1% BSA (this buffer solution is hereinafter designated as buffer solution B). The gel suspension was stored overnight at 4° C.

The whole volume of the suspension was packed in a column and the column was successively washed with 250 ml of buffer solution B, 250 ml of buffer solution B containing a protease inhibitor (a mixture of EDTA, trypsin inhibitor, phenylmethylsulfonyl fluoride, iodoacetate, ε-aminocaproic acid, benzamidine and pepstatin), and 3M NaCl solution. Thereafter, the adsorbate was eluted with buffer solution A and recovered.

The recovered adsorbate was concentrated to such an extent that an ultraviolet light (280 nm) absorbance of at least 0.2 was obtained.

The concentrate was distributed into vials and stored frozen to prepare reagents of biotin-hyaluronic acid coupling protein complex.

Assaying High Molecular Hyaluronic Acid

Fifty microliters of a NaHCO$_3$ solution of the purified hyaluronic acid binding protein at a concentration of 20 μg/ml was uniformly coated on a Falcon plate (Becton Dikinson) and stored overnight at 4° C.

The surface of the Falcon plate that had been covered with the hyaluronic acid binding protein was covered with a blocking substance that was added in the form of 0.5% bovine γ-globulin in solution. The plate was then stored at room temperature for 2 hours.

After washing the plate 3 times with a 0.85M NaCl solution containing 0.05% Tween 20, 50 μl of a standard sample that was a 1:11 dilution of serum containing 10 ng/ml of high molecular hyaluronic acid was added to the plate and stored at room temperature for 2 hours. It was confirmed that equally good results could be attained by adding a sample of hyaluronic acid using a solution of blocking material instead of serum.

The plate was subsequently washed 3 times with a 0.85M NaCl solution containing 0.05% Tween 20 and the previously prepared biotin-hyaluronic acid binding protein complex (diluted to 1:300 with the solution of 0.5% bovine γ-globulin as a blocking material) was added in an excess amount over hyaluronic acid. The plate was stored at room temperature for 2 hours.

Thereafter, the plate was washed 3 times with a 0.85M NaCl solution containing 0.05% Tween 20 and avidin-POD (VECTOR) diluted 1:3000 with the solution of 0.5% bovine γ-globulin as a blocking material was added. The plate was then stored at room temperature for 45 minutes.

The plate was washed 3 times with a 0.85M NaCl solution containing 0.05% Tween 20 and 100 μl of a solution of 2 mg/ml of ortho-phenylenediamine (Nakarai Kagaku Co., Ltd.; containing 0.015% H$_2$O$_2$, 0.018M citric acid, 0.064M sodium hydrogenphosphate, and 0.1% salicylic acid) was added. The plate was then stored at room temperature for 30 minutes. Thereafter, the decomposition of ortho-phenylenediamine was terminated by adding of 8N H$_2$SO$_4$ in two drops.

The reaction solution colored by decomposition of ortho-phenylenediamine was assayed for absorbance at 492 nm with a spectrophotometer.

Additional samples were prepared by the procedures described above for standard hyaluronic acid concentrations of 50, 100, 500 and 1,000 ng/ml. The absorbance at 492 nm of the color produced by decomposition with ortho-phenylenediamine was measured with a spectrophotometer. The results are shown in FIG. 1, from which one can see that the assay method of the present invention is capable of detecting and quantifying a high molecular hyaluronic acid to limit of the order of 10 ng.

If one wants to measure the blood level of a high molecular hyaluronic acid for the purpose of diagnosing inflammations such as rheumatism or diseases such as cancer, it is appropriate to employ a reagent kit consisting of suitable containers containing a labelled hyaluronic acid binding protein, a solid-phase adsorbed hyaluronic acid binding protein, and a standard sample containing a high molecular hyaluronic acid, all of these reagents being prepared by the procedures described herinbefore, as well as a solid phase such as a plate, tube, bead, membrane in gel.

As will be understood from the foregoing description, the method of the present invention is capable of selectively assaying a high molecular hyaluronic acid without responding to unwanted low molecular species. Since this method does not depend on a competitive reaction for assaying hyaluronic acid, it does not require a purified form of hyaluronic acid as a reagent and permits as small as 10 ng of a high molecular hyaluronic acid to be detected or quantified by a very simple operation.

Because of these features, the assay method of the present invention is of great value in clinical applications and can be effectively used in the diagnosis of inflammations such as rheumatism or diseases such as cancer.

What is claimed is:

1. A method of assaying a high molecular hyaluronic acid having at least two sites available for coupling to a hyaluronic acid binding protein comprising the following steps: adding a sample containing a hyaluronic acid of interest to a first hyaluronic acid binding protein that is absorbed on a solid phase, thereby permitting the first absorbed hyaluronic acid binding protein to bind to the hyaluronic acid of interest; further adding either a second hyaluronic acid binding protein and a marker or a second hyaluronic acid binding protein labelled with a marker, said first hyaluronic acid binding protein being the same as said second hyaluronic acid binding protein, thereby forming a complex of sandwich structure in which the haluronic acid of interest is held between the solid phase adsorbed hyaluronic acid binding protein and the labelled hyaluronic acid binding protein; and measuring the quantity of said hyaluronic acid of interest in terms of the marker in said complex.

2. A method according to claim 1 wherein the surface of the solid phase on which the hyaluronic acid binding protein has been adsorbed is subsequently treated with a blocking substance in such a way that the area of said solid phase of which the hyaluronic acid binding protein is not adsorbed is covered with said blocking substance.

3. A method according to claim 1 wherein said solid phase is one member selected from group consisting of a plate, a tube, beads, a membrane and a gel.

4. A method according to claim 1 wherein said hyaluronic acid binding protein is one member selected from the group consisting of a proteoglycan, a link protein and a hyaluronectin.

5. A method according to claim 1 wherein said marker is one member selected from the group consisting of an isotope, a flourochrome, avidin, biotin, a chemoluminescent substance and an enzyme.

6. A method according to claim 2 wherein said blocking substance is one member selected from the group consisting of γ-globulin, serum albumin and serum.

7. A kit of reagents for assaying a high molecular hyaluronic acid having a t least two sites available for coupling with a hyaluronic acid binding protein which comprises as constituent elements in suitable containers therefore a labelled hyaluronic acid binding protein, a hyaluronic acid binding protein adsorbed on a solid phase, and a standard sample containing a high molecular hyaluronic acid.

8. A kit according to claim 7 wherein the surface of the solid phase on which the hyaluronic acid binding protein has been adsorbed is subsequently treated with a blocking substance in such a way that the area of said solid phase on which the hyaluronic acid binding protein is not adsorbed is covered with said blocking substance.

9. A kit according to claim 7 wherein said solid phase is one member selected from the group consisting of a plate, a tube, beads, a membrane and a gel.

10. A kit according to claim 7 wherein said hyaluronic acid binding protein is one member selected from the group consisting of a proteoglycan, a link protein and a hyaluronectin.

11. A kit according to claim 7 wherein said marker is one member selected form the group consisting of an isotope, a fluorochrome, avidin, biotin, a chemoluminescent substance and an enzyme.

12. A kit according to claim 8 wherein said blocking substance is one member selected from the group consisting of γ-globulin, serum albumin and serum.

* * * * *